(12) United States Patent
Kwek et al.

(10) Patent No.: US 8,014,852 B2
(45) Date of Patent: Sep. 6, 2011

(54) SYSTEM, METHOD AND APPARATUS FOR DETECTING A CARDIAC EVENT

(76) Inventors: Alfred Tai Chuan Kwek, Singapore (SG); Narayan Nimbkar, Hanover, MA (US)

(*) Notice: Subject to any disclaimer, the term of this patent is extended or adjusted under 35 U.S.C. 154(b) by 975 days.

(21) Appl. No.: 11/666,326

(22) PCT Filed: Oct. 25, 2005

(86) PCT No.: PCT/SG2005/000366
§ 371 (c)(1),
(2), (4) Date: Oct. 8, 2007

(87) PCT Pub. No.: WO2006/046930
PCT Pub. Date: May 4, 2006

(65) Prior Publication Data
US 2008/0064972 A1 Mar. 13, 2008

Related U.S. Application Data

(60) Provisional application No. 60/621,044, filed on Oct. 25, 2004.

(51) Int. Cl.
*A61B 5/0452* (2006.01)
(52) U.S. Cl. ........................................... 600/517
(58) Field of Classification Search .................. 600/517, 600/509, 516
See application file for complete search history.

(56) References Cited

U.S. PATENT DOCUMENTS

| 3,616,791 | A |   | 11/1971 | Harris |         |
|-----------|---|---|---------|--------|---------|
| 4,181,135 | A |   | 1/1980  | Andresen et al. | |
| 4,316,249 | A | * | 2/1982  | Gallant et al. | 600/515 |
| 5,400,795 | A | * | 3/1995  | Murphy et al. | 600/515 |

FOREIGN PATENT DOCUMENTS

| EP | 0 512 719 A2 | 11/1992 |
| EP | 0 745 942 A2 | 12/1996 |

OTHER PUBLICATIONS

Ginefra et al., "Detection of Incipient Left Ventricular Hypertrophy in Mild to Moderate Arterial Hypertension with Normal Electrocardiogram and Echocardiogram. A New Use for Signal-Advanced Electrocardiography," *Arq Bras Cardiol*, 2003, 81(1):79-84.

(Continued)

*Primary Examiner* — Eric D. Bertram
(74) *Attorney, Agent, or Firm* — Jones Day; Nicola A. Pisano

(57) ABSTRACT

A system, method and apparatus for detecting a cardiac event in a subject, may include at least one electrode attached to the subject for obtaining an electrocardiogram of the subject's heart, and determination means for determining a size of an area under a QRS complex of the electrocardiogram. The at least one electrode may be attached to the subject's skin or to the subject's heart. Preferably, the determination means for determining the size of the area under the QRS complex of the electrocardiogram is either visual or quantitative. The subject may be a human being or an animal. The size of the area under the QRS complex of the electrocardiogram determined by the determination means is directly proportional to the mass of a viable myocardium in the subject's heart. The cardiac event that may be detected may be degenerative cardiomyopathy, acute myocardial infarction, arrhythmia, myocardial ischaemia, or compromised ventricular function.

26 Claims, 14 Drawing Sheets

OTHER PUBLICATIONS

Okin et al., "Time-Voltage Area of the QRS for the Identification of Left Ventricular Hypertrophy," *Hypertension*, 1996, 27:251-258.

Okin et al., "Time-Voltage QRS Area of the 12-Lead Electrocardiogram. Detection of Left Ventricular Hypertrophy," *Hypertension*, 1998, 31:937-942.

Molloy, Thomas J. et al., "Electrocardiographic Detection of Left Ventricular Hypertroply by the Simple QRS Voltage-Duration Project," *JACC*, 1992, 20(5):1180-6.

Office Communication in corresponding EP Patent Application No. 05795689.8.

* cited by examiner

SYSTEM, METHOD AND APPARATUS FOR DETECTING A CARDIAC EVENT

CROSS REFERENCE TO RELATED APPLICATION

This application is a national phase application of International Patent Application No. PCT/SG2005/000366, filed Oct. 25, 2005, which claims priority from U.S. Provisional Appln. No. 60/621,044 filed Oct. 25, 2004 the entire contents of which are expressly incorporated herein by reference.

FIELD OF INVENTION

This invention relates to a system, method and apparatus for detecting a cardiac event.

BACKGROUND

Chest pain is a very common and a complex symptom that medical practitioners need to accurately diagnose on a daily basis. The diagnosis for patients with chest pain range from myocardial spasms to acute myocardial infarction (AMI). An accurate and correct diagnosis saves lives while misdiagnosis may lead to serious morbidity and mortality to the patient. Medical practitioners rely on their experience and diagnostic tools such as, for example, electrocardiography (ECG), serum markers, ionizing radiation, dobutamine stress echocardiography (DSE), single photon emission computed tomography (SPECT), positron emission tomography (PET) and magnetic resonance imaging (MRI) to furnish a diagnosis on a patient's condition. Unfortunately, medical practitioners invariably face the risk of malpractice actions being started against them subsequent to their failure to diagnose a patient correctly. This is disturbing for the medical practitioners, especially when their diagnostic tools are constrained in their capabilities.

There are currently limitations in relation to the use of serum markers. The more notable limitations relate to: (i) no single determination of one serum biochemical marker of myocardial necrosis reliably identifies or reliably excludes AMI less than six hours of symptom onset; (ii) no serum biochemical marker identifies or excludes unstable angina at any time after symptom onset; and (iii) the lack of diagnostic sensitivity of point-of-care devices resulting in the overlooking of elevations of cardiac troponin levels.

Similarly, there are also limitations in relation to the use of twelve lead ECGs. These limitations include: deciphering atypical electrocardiograms of patients with AMIs, inaccurate static analysis of a dynamic process like AMI, and the fact that electrocardiograms are more like prognostic (predictive) tools rather than diagnostic tools.

There is currently no known disclosure of the use of ECGs to quantify the mass of viable myocardium in the heart. Current methods of quantifying viable myocardium are not ideal. Techniques, such as, for example, SPECT, DSE, and PET, are unable to measure the direct presence and exact quantity of viable myocytes. In SPECT and PET, inaccuracies arise due to poor spatial resolution. Likewise, in DSE, inaccuracies arise because of errors in registration between comparison images, and an inability to visualize all parts of the left ventricular myocardium. At the present moment, an MRI may be used for the determination of infarct size, assessment of myocardial viability and assessment of myocardial ischaemia. However, MRI costs are still rather prohibitive, consequently restricting their availability to well funded medical institutions.

It is well-known that although most akinetic segments of ventricular myocardium correspond to infarcted regions, a variable amount of myocytes survive the acute ischaemic insult and remain at risk as critical narrowing or occlusion of the infarct vessel, in most cases, persists without intervention. The survivability of myocardium depends on residual perfusion, energy demands, and the metabolic and hormonal environment, among other factors. Detecting viable myocardium is of significant clinical relevance for a number of reasons. Firstly, a region may recover contractile function, at least to some extent, and thereby not only improve symptoms of heart failure, but also reduce morbidity and mortality. Secondly, viable myocardium in a critically perfused region may represent a substrate for life-threatening arrhythmia. Thirdly, residual viability in akinetic regions tends to disappear gradually, even without recurrence of an acute coronary event (this is significant as operative mortality in coronary patients with poor ventricular function is lower in the presence of viable myocardium, and timely intervention may further reduce the risk). Finally, preservation of even a small layer of viable myocardium in an infarcted region may prevent progressive remodeling and failure. Thus, assessment of tissue viability allows for better stratification of coronary patients with compromised left ventricular function, and improves the selection of high-risk patients for invasive procedures.

SUMMARY OF THE INVENTION

The present invention is to provide a remedy for the above-discussed disadvantages. It is an object of the invention to create a system for detecting a cardiac event in a subject, including: at least one electrode attached to the subject for obtaining an electrocardiogram of the subject's heart; and means for determining a size of an area under a QRS complex of the electrocardiogram. At least one electrode may be attached to the subject's skin or to the subject's heart. Preferably, the means for determining the size of the area under the QRS complex of the electrocardiogram is either visual or quantitative. The subject may be a human being or an animal.

It is advantageous that the size of the area under the QRS complex of the electrocardiogram is directly proportional to the mass of viable myocardium in the subject's heart. The cardiac event that may be detected may be degenerative cardiomyopathy, acute myocardial infarction, arrhythmia, myocardial ischaemia, or compromised ventricular function.

The quantifiable difference between the size of the area of the QRS complex of the electrocardiogram and a size of an area of a QRS complex of an electrocardiogram from the same subject obtained at a prior occasion from identical leads may advantageously show a change in the mass (gain or loss) of viable myocardium in the subject's heart over a period of time. No significant change in the mass of viable myocardium may also be shown. The means for determining the difference may be either visual or quantitative.

There is also provided a method for detecting a cardiac event in a subject, including: attaching at least one electrode to the subject for obtaining an electrocardiogram from the subject's heart; and determining a size of an area under a QRS complex of the electrocardiogram. The at least one electrode may be attached to the subject's skin or to the subject's heart. It is preferable that the size of the area under the QRS complex of the electrocardiogram is determined using visual or quantitative means.

There is also disclosed an apparatus for carrying out a method for detecting a cardiac event in a subject.

There is also disclosure of a system for generating an index for ascertaining an onset of a cardiac event in a subject, including: at least one electrode attached to the subject for obtaining an electrocardiogram from the subject's heart; a means for determining a size of an area under a QRS complex of the electrocardiogram; a means for obtaining a difference between the size of the area of the QRS complex of the electrocardiogram and a size of an area of a QRS complex of an electrocardiogram from the same subject obtained at a prior occasion from identical leads; and a means for obtaining a quotient of the difference and the size of an area of a QRS complex of the electrocardiogram from the same subject obtained at the prior occasion. The index results from the difference and the quotient being directly proportionate to one another.

It is preferable that when determining the index, the means for determining the size of the area under the QRS complex of the electrocardiogram, the means for obtaining the difference between the size of the area of the QRS complex of the electrocardiogram and a size of an area of a QRS complex of an electrocardiogram from the same subject obtained at a prior occasion, and the means for obtaining a quotient of the difference and the size of an area of a QRS complex of the electrocardiogram from the same subject obtained at the prior occasion are quantitative.

A corresponding method for generating an index for ascertaining an onset of a cardiac event in a subject is also disclosed.

BRIEF DESCRIPTION OF DRAWINGS

The present invention is explained in even greater detail in the following exemplary drawings. The present invention may be better understood by reference to the following drawings, wherein like references numerals represent like elements. The drawings are merely exemplary to illustrate the structure, operation and method of use of the present invention and certain features that may be used singularly or in combination with other features and the invention should not be limited to the embodiments shown.

The invention is explained in more detail schematically and by way of example with reference to figures.

DESCRIPTION OF PREFERRED EMBODIMENTS

Figure 1:
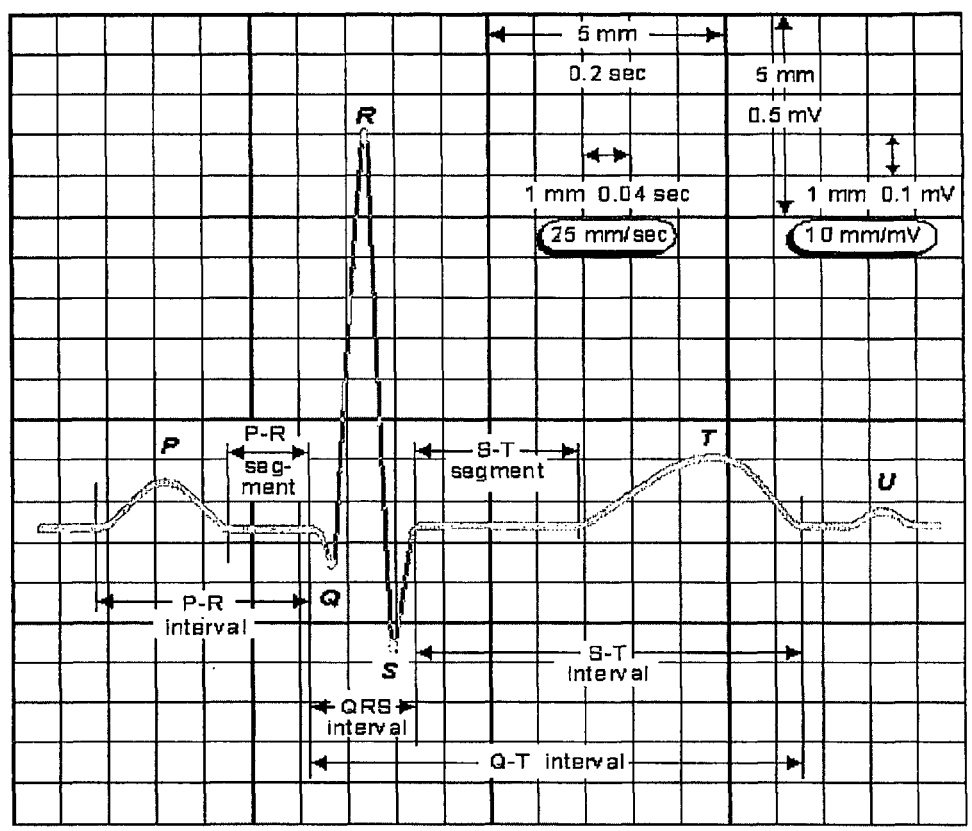
FIG. 1 shows an ECG rhythm strip.

In order to better understand the preferred embodiment of the present invention, there is provided additional information on electrocardiographic (ECG) background and nomenclature. The ECG is a test that reveals more about heart rhythm, size/function of chambers of a heart, and of the heart muscle. A healthy heart's electrocardiogram demonstrates a predictable pattern. When there are changes in the condition of the heart, discernible changes will correspondingly show up on an electrocardiogram. The ECG is a non-invasive, visual representation of the electrical characteristics of a heartbeat derived from low-level electrical impulses passing through twelve wires (or leads) placed at standardized locations on the skin. However, it is to be noted that this invention is not restricted for use with twelve-lead ECG systems. The ECG is performed to obtain clinical information about cardiac function and serves as a permanent graphical record of the heart's overall response to the millions of tiny currents flowing within and between the heart's individual cells. With experience and training, an observer may infer important information about a heart's condition. Referring to FIG. 1, the undulations or "waves" of each heartbeat (or a single cardiac cycle) are labeled as shown on an ECG rhythm strip. The labeling is done in accordance to long accepted convention, with the use of letters P, Q, R, S, T and U.

The first four waves: P, Q, R and S, represent passive current flows akin to the discharge of a battery (or more accurately, a capacitor) firing a spark plug. The first wave, P, represents the synchronous depolarisation (discharge) of the cells of the atria (the upper chambers of the heart), which propel blood into the ventricles (the main pumping chambers of the heart) just like the priming of a pump. The second, third and fourth (Q, R and S) waves represent a synchronized discharge, or "firing," of the cells of the right and left ventricles, initiating the process of pumping blood to the lungs and to the rest of the body, respectively. The final two waves, T and U, represent active, energy-consuming, metabolic processes similar to recharging a battery or capacitor.

The duration between the various waves may be interpreted to represent different portions of a cardiac cycle. For example, a time interval from a peak of one R wave to a peak of a subsequent R wave (RR interval) represents the duration of one cardiac cycle (one heartbeat). The PR interval represents the time for depolarisation of the atria (to prime the pump), and the QRS interval represents the time required to "fire" the main pumping chambers.

Figure 2:
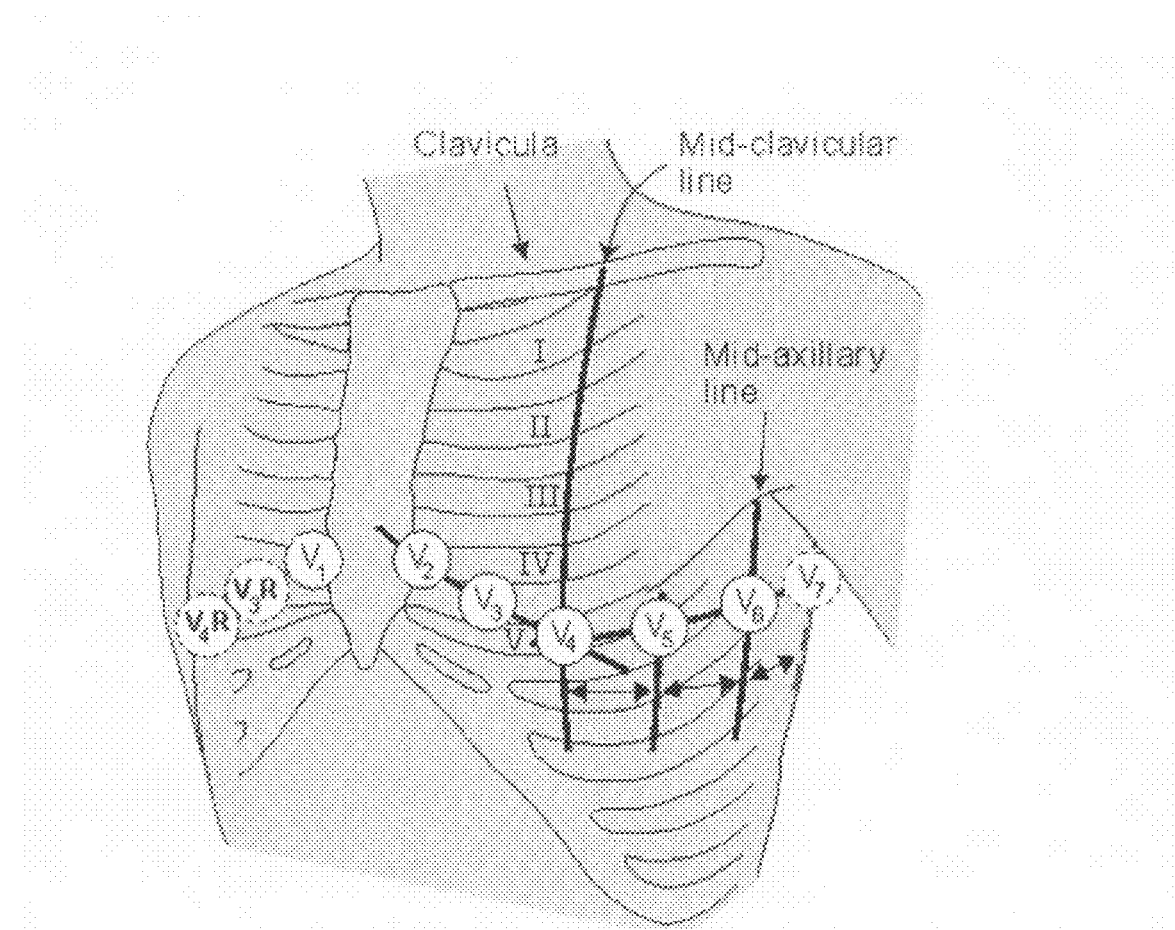
FIG. 2 shows a standard positioning for a twelve lead ECG system.

Electrocardiographic signals may be measured at any point on the body surface. The signal magnitude on the torso in normal healthy adults is around 5 mV and is relatively easily detectable. The morphology of the electrocardiographic signals depend on the cardiac generators, the volume conducting medium, and the location of the pickup electrodes (leads) at the surface of the body. The location of the leads may be established to fulfil some theoretical consideration such as in the case of orthogonal lead systems, or defined by anatomical landmarks such as, for example, the clavicula, the sternum, and so forth, so that the variation from geometry is minimised by adopting a standard lead arrangement as shown in FIG. 2. Even though a cardiac cycle produces electrocardiographic signals with differing morphology among the different leads because of differences in lead location, a relationship exists since the source and volume conductor are the same for all leads. A lead vector provides a quantitative description of the relationship between the source and the lead voltage as affected by the lead location.

The QRS complex is recorded on the electrocardiograph at an instance when the heart is undergoing ventricular depolarisation and atrial repolarisation. Due to the large number of ventricular cells and small number of atrial cells participating in electric events, ventricular electrical vector predominates with the electric field and isopotential contours changing correspondingly. As the depolarisation waves moves from the endocardial to the epicardial surfaces of the myocardium, potentials of relatively high voltages are recorded. These potentials consist of some combination of Q, R and S waves and are collectively referred to as the QRS complex. The QRS complex represents ventricular depolarisation. The potentials of atrial polarisation are small and are buried within the QRS complex.

Similarly, the mathematical quantification of a mass of viable myocardium in a heart using an area defined by the QRS complex is explained here to better understand the preferred embodiment of the present invention.

Figure 3:
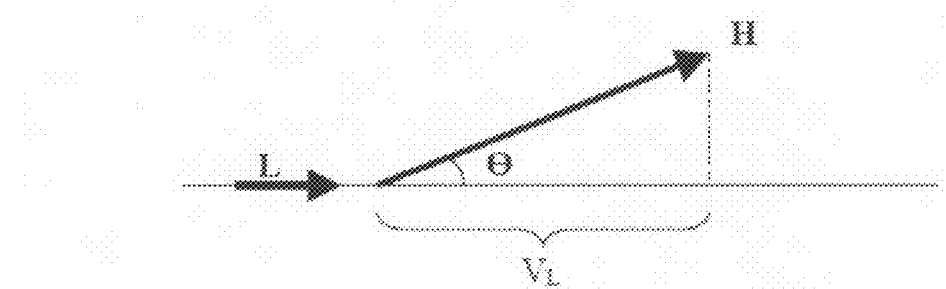
FIG. 3 shows a diagram of a projection of a heart vector on a lead vector.

Referring to FIG. 3, there is shown a diagram of a projection of a heart vector on a lead vector. An amplitude and polarity of the potentials sensed in an ECG lead equals the projection of the heart vector, H on the lead vector, L in the direction of the lead vector L. As such:

$$V_L = \int H \int \cos \Theta \int L \int$$

where
- $V_L$ = amplitude in V lead;
- H = heart vector;
- $\Theta$ = the angle between the heart vector and the lead vector;
- L = the lead vector (unit vector), which is a line joining the center of torso with the placement site of the V lead; and
- $\int L \int = 1$.

Figure 4:
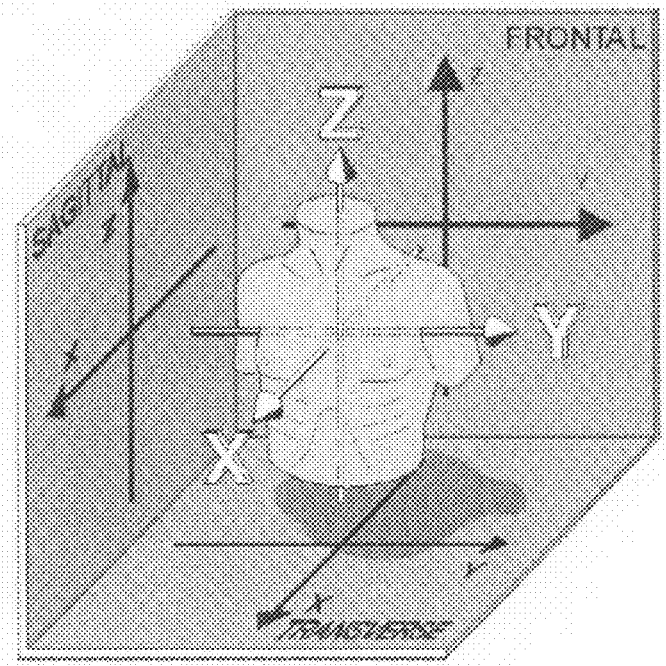
FIG. 4 shows a diagram of an orthogonal coordinate system.

The projection of the instantaneous potentials H generated is plotted as an ECG tracing with time as the other variable. The frame of reference for the ECG tracing is the X-axis which is a line joining the precordial lead placement site and the center of torso. Referring to FIG. 4, a system of X, Y, Z axes orthogonal to each other is shown such that the Y axes is directed orthogonally on the same plane as the horizontal X axes, and the Z axis directed orthogonally to both. All three axes intersect at the centre of the torso.

It should be noted that for a heart that has not suffered from any cardiomyopathy, areas under QRS complexes when t=0 and t=1 remains the same despite deliberate alterations in electrode positions. While leads may be positioned at anatomical landmarks in a well-defined and consistent manner (standard lead system), variations in leads positions at t=0 and t=1 introduces significant errors into the areas under the QRS complexes obtained using this invention. Hence, there is an assumption that there is no reduction in viable myocardium at both t=0 and t=1.

Figure 5:
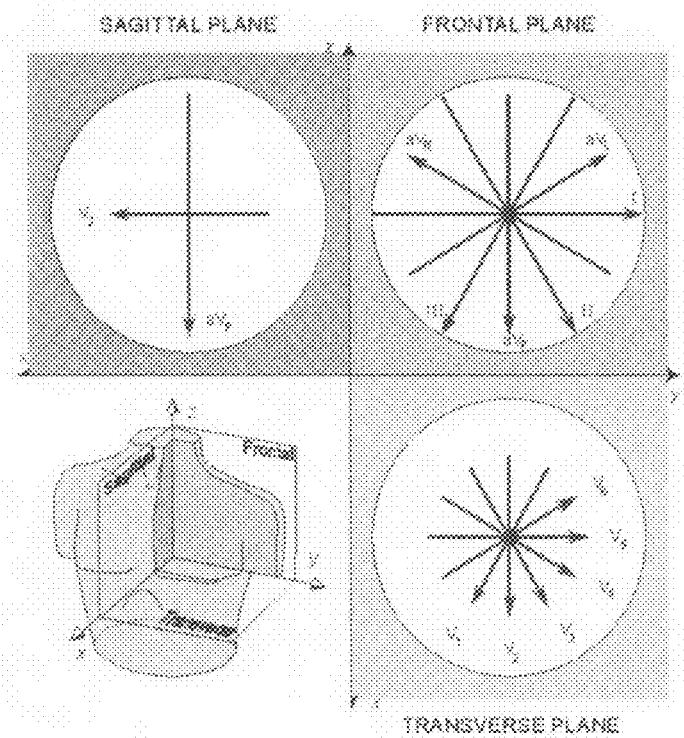
FIG. 5 shows projections of lead vectors in three orthogonal planes.

Referring to FIG. 5 which shows lead vectors for each lead based on an idealized (spherical) volume conductor, a precordial site does not have a big curvature of chest wall and hence the change in projection on Z axis of the points two cm above and below respectively on the chest wall is close to zero which is the projection of the lead site itself. The projection of the electrical potential vector on the X-axis which is the ECG tracing is maximum and does not change significantly with rotation of the X-axis either above or below because the angle of rotation is small. The rotation of the reference frame by, for example, angle α, around Z-axis will change the projection of the Vector on the new axial system. This changes the ECG morphology. The change in morphology may be quite obvious even though the total contribution of the generated potential to the ECG remains almost the same. The reason for the minimal change in the scalar quantity is the factor cos α, which for a small angle approximates to one. Even if the original frame of reference had an angle Θ between the electrical vector and the axis of reference (from center of torso to the site of lead placement), cos(Θ+α)=cos Θ cos α−sin Θ sin α, for very small angles is close to 1.0. The translocation of both X and Y axes either superiorly or inferiorly does not change the respective projections on the X or Y-axes. The change in morphology as one shifts the leads above or below is dependent upon the relationship of three reference lines namely:

- center of torso to normal lead site;
- center of torso to displaced lead site; and
- directional line of the spread of electrical potential, the electrical vector.

Figure 12:
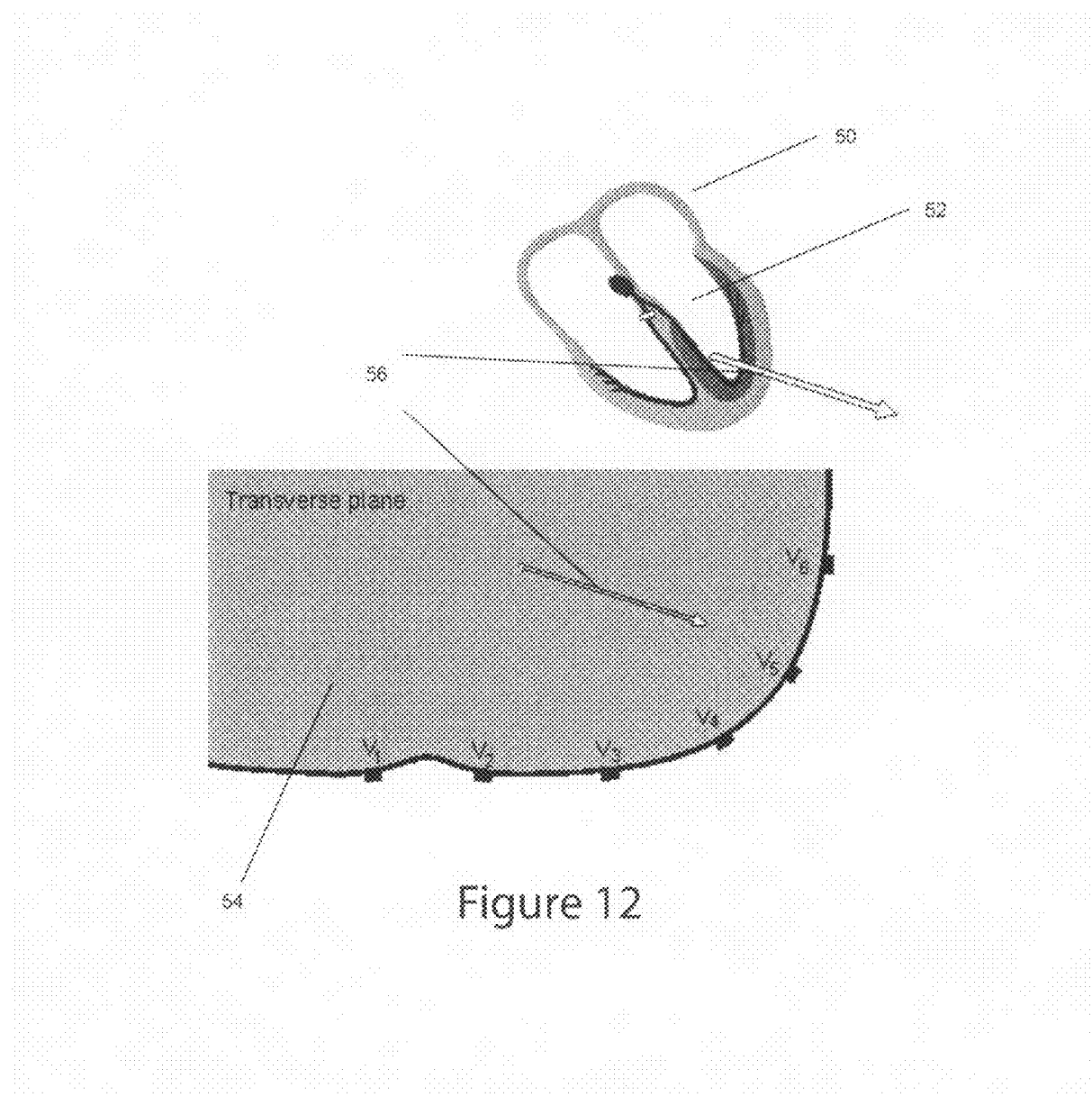
FIG. 12 shows the positioning of leads in relation to a heart in a transverse plane.

It is suggested that despite the morphologically different QRS complexes with the shift in the precordial leads, the integration, ∫QRS dt, which represents the mass of myocardium generating the electrical potentials of activation, remains unchanged. It is also important to note that sometimes the change in morphology is seen in leads V4, V5 and V6 by upward and/or downward displacement by a small distance. FIG. 12 shows how the positioning of leads V4, V5 and V6 in a transverse view allows for the readings to be taken from a left ventricle 52 of a heart 50. Leads V4, V5 and V6 are seen to be positioned ideally to be able to obtain readings from the left ventricle 52 of the heart. It is however possible that in pathologically altered configurations of the heart (e.g. right or left ventricular hypertrophy anatomical shifts in position of the heart), similar changes may be observed in the other precordial leads.

Out of the twelve leads, the first six are derived from the same three measurement points. Therefore, any two of these six leads include exactly the same information as the other four. It is known that over 90% of the heart's electric activity can be explained with a dipole source model. To evaluate this dipole, it is adequate to measure its three independent components where two of the limb leads could reflect the frontal plane components, whereas one precordial lead could be chosen for the anterior-posterior component. The combination should adequately describe the electric heart vector.

Either one of leads V4, V5 or V6 would be a very good precordial lead choice since it is directed closest to the left ventricle 52 of the heart. It is roughly orthogonal to the standard limb plane, which is close to the frontal plane. To the extent that the cardiac source can be described as a dipole, the twelve lead ECG system could be thought to have three independent leads and nine redundant leads. However, the precordial leads also detect non-dipolar components, which have diagnostic significance because they are located close to the frontal part of the heart. Therefore, the twelve lead ECG system actually has eight truly independent and only four redundant leads.

The main reason for recording all twelve leads is historical and that it enhances pattern recognition. This combination of leads gives a practitioner an opportunity to compare the projections of the resultant vectors in two orthogonal planes and at different angles. This is further facilitated when the polarity of the lead $aV_R$ can be changed with the $-aV_R$ lead being included in many ECG recorders.

Figure 6:
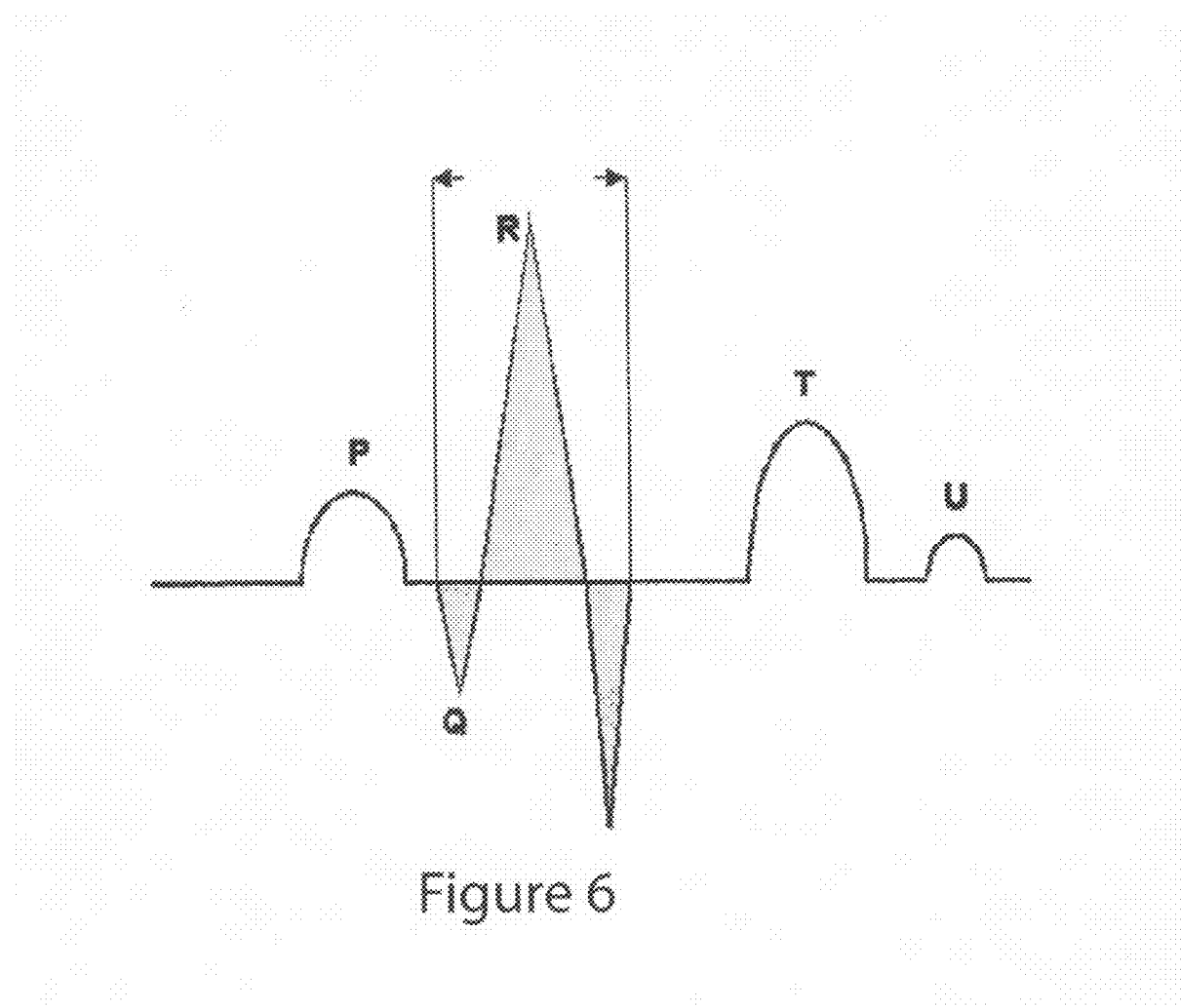
FIG. 6 shows reproduction of the electrocardiogram of FIG. 1.

In one embodiment, a system for detecting a cardiac event in a subject is provided. The subject may be a human being or an animal. The system includes the attachment of at least one electrode to the subject for obtaining an electrocardiogram of the subject's heart. The at least one electrode may be attached to the subject's skin or directly to the subject's heart. Referring to FIG. 12, leads V4, V5 and V6 are seen to be positioned ideally to be able to obtain readings from the left ventricle 52 of the heart, with respect to the chest cavity 54, and each lead may be used independently to obtain the electrocardiogram of the subject's heart. Dipole 56 illustrates the direction of the electrical dipole generated by the heart in the chest cavity 54, as seen by the leads V4, V5 or V6. The positioning of the electrodes on the chest is per standard convention for the attainment of an electrocardiogram. Subsequent to the attainment of the electrocardiogram, a size of an area under a QRS complex of the electrocardiogram is determined to ascertain a mass of viable myocardium in the subject's heart. This may be possible as the size of the area under the QRS complex of the electrocardiogram is directly proportional to the mass of viable myocardium in the subject's heart. FIG. 6 shows a reproduction of the electrocardiogram of FIG. 1. The size of the area under the QRS complex of the electrocardiogram may be determined using visual and/or quantitative. The area under the QRS complex of the electrocardiogram is denoted by the shaded regions in FIG. 6.

The quantification of the mass of viable myocardium in the heart is done by integrating the QRS complex of an electrocardiogram to obtain the area under the QRS complex. As mentioned earlier, the Q, R and S waves represent the depolarisation, or discharge, of the myocardium cells in the right and left ventricles. This process of depolarisation initiates myocardium contraction of the right and left ventricles, thus commencing the process of pumping blood to the lungs and to the rest of the body, respectively. As the QRS complex is produced by ventricular depolarization, the magnitude of depolarization is proportional to the mass of myocardium generating it. Thus, integration of the instantaneous depolarization is proportional to the total myocardial mass. Correspondingly, determining a difference between the size of the area of the QRS complex of the electrocardiogram and a size of an area of a QRS complex of an electrocardiogram from the same subject obtained at a prior occasion shows change in the mass of viable myocardium in the subject's heart over that period of time. An increase in the area from an earlier electrocardiogram from an identical lead(s) shows an increase in the mass of viable myocardium while a decrease in area shows a decrease in the mass of viable myocardium. Similarly, a minimal change in the area from an earlier electrocardiogram also shows an insignificant change in the mass of viable myocardium in the subject's heart. For example, by comparing the areas under the QRS complexes of a pre-infarct and post-infarct heart, practitioners may be able to determine whether the infarct heart has: suffered a loss of viable myocardium, and a smaller mass of viable myocardium remaining after the infarct, when compared to prior the infarct. It is foreseeable that practitioners need not refer to electrocardiograms of their patients from earlier occasions if they are familiar with the medical history of their patients.

Figure 7:
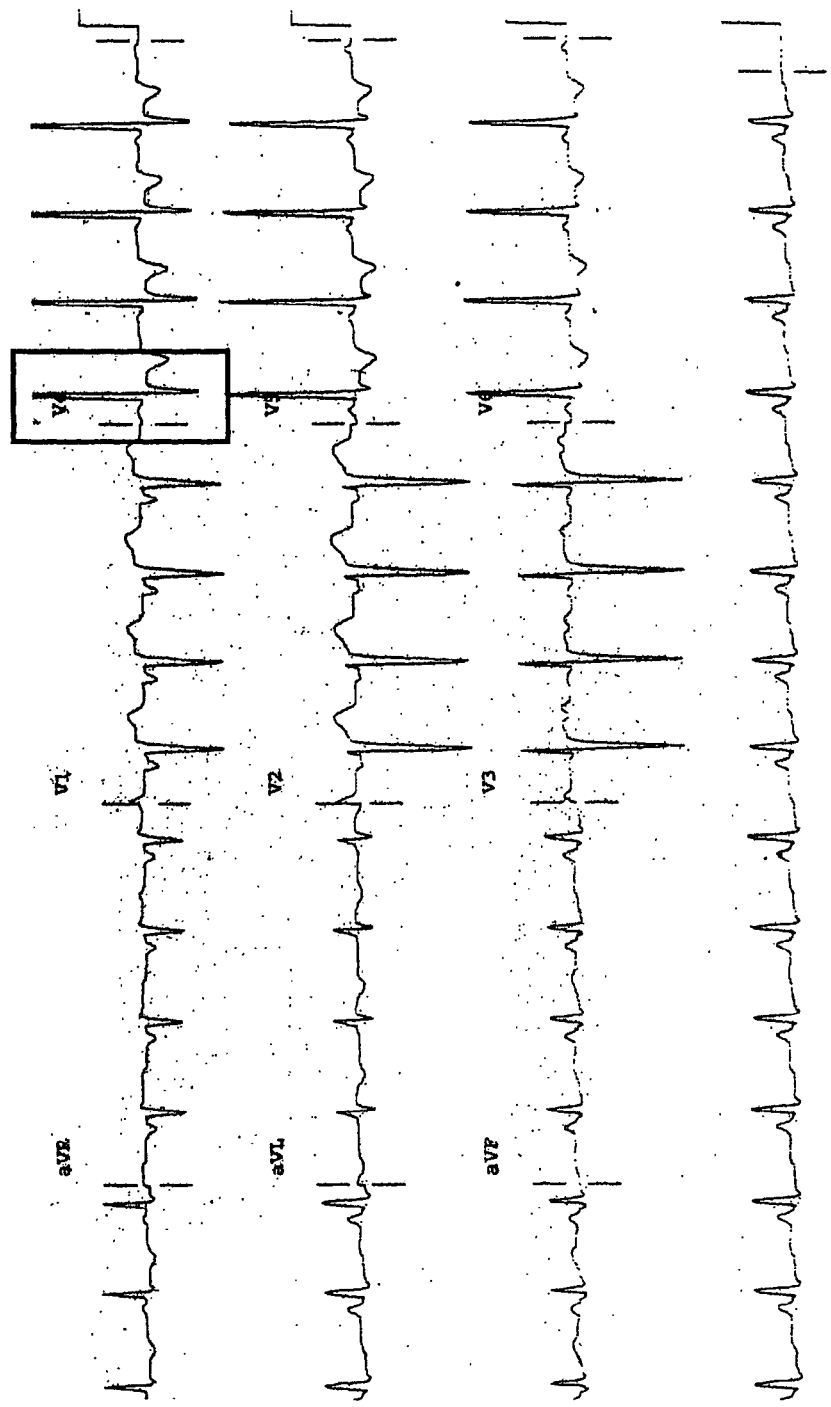
FIG. 7 shows a demonstrative ECG of patient A taken on 26 Dec. 2003.
Figure 8:
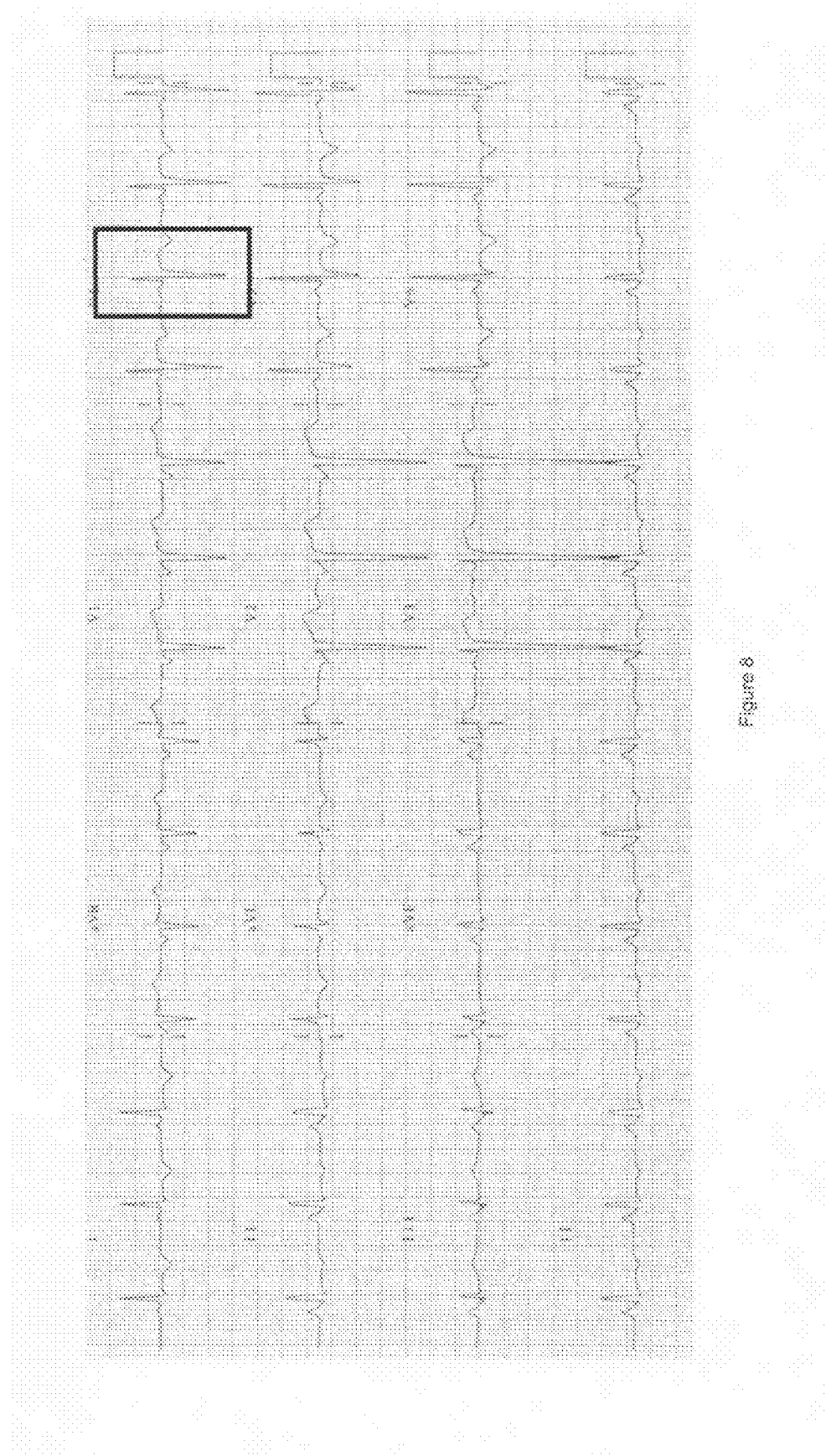
FIG. 8 shows a demonstrative ECG of patient A taken on 18 May 2005.
Figure 9:
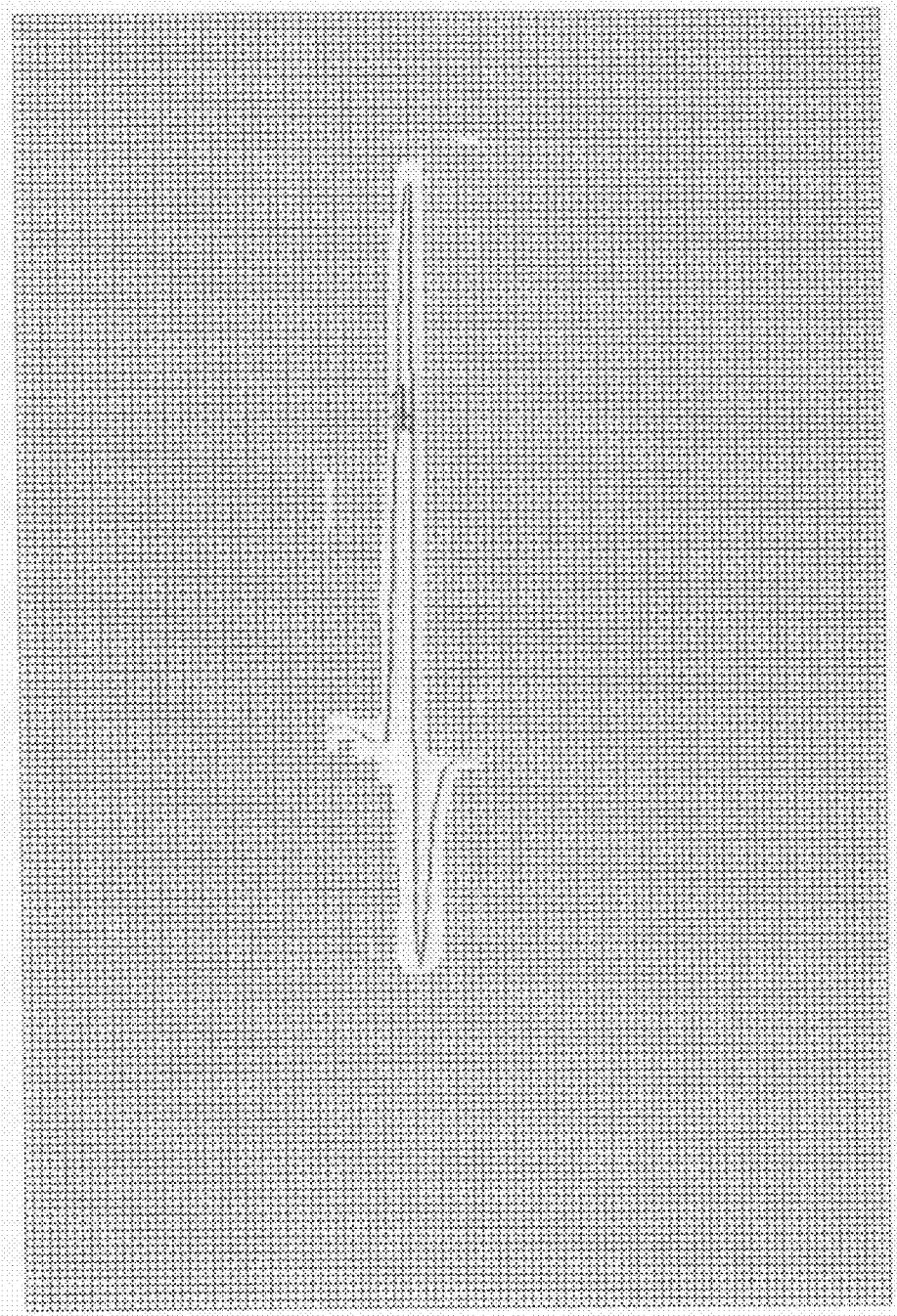
FIG. 9 shows an enlarged portion of the boxed portion, denoting lead V4, of the ECG of FIG. 7.
Figure 10:
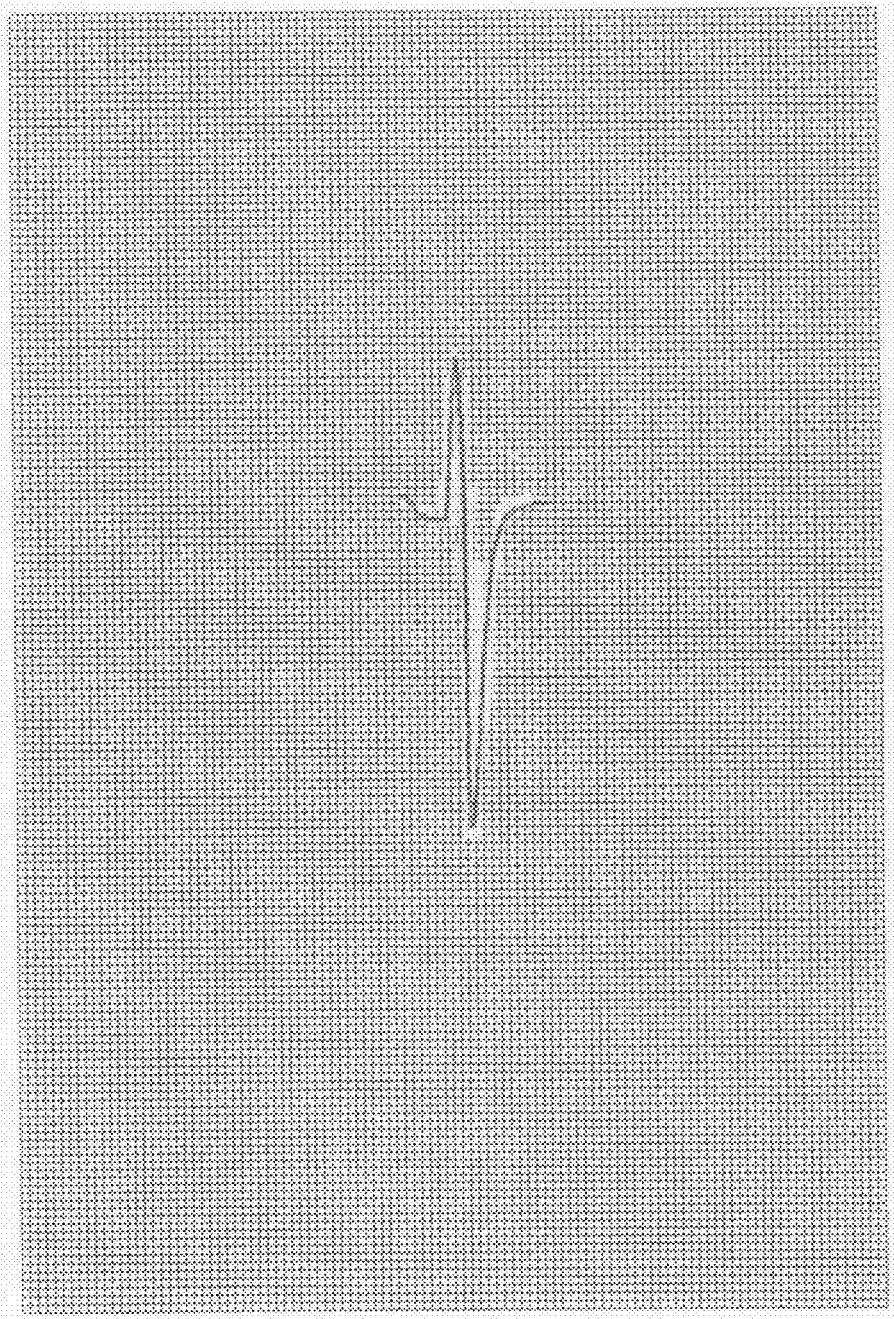
FIG. 10 shows an enlarged portion of the boxed portion, denoting lead V4, of the ECG of FIG. 8.

FIGS. 7 to 10 show actual ECGs of a patient. FIG. 8 shows the ECG at time t=1 (the more recent measurement when patient was aged 66), while FIG. 7 shows the ECG at time t=0 (the earlier measurement when patient was aged 64). FIG. 9 shows an enlarged graph (by 700%) of the boxed QRS region for lead V4 in FIG. 7 while FIG. 10 shows an enlarged graph (by 700%) of the boxed QRS region for lead V4 in FIG. 8. By reviewing FIGS. 9 and 10, it is evident that the area under the QRS has decreased just by looking at the figures. Clinical diagnosis revealed that the patient has suffered an ischaemic insult. From a count of the squares in FIGS. 9 and 10, it can be shown quantitatively that:

$$\text{(Area under curve at } t=1\text{)}-\text{(Area under curve at } t=0\text{)}= 95\text{-}194 \text{ mm}^2 = -99 \text{ mm}^2$$

A negative area means that there's a reduction in area under the QRS curve which corresponds to a loss of viable myocardium. Hence, even without experience and training, an observer may be able to quantify the mass of viable myocardium which provides an important and accurate indicator of a heart's health.

Figure 11:
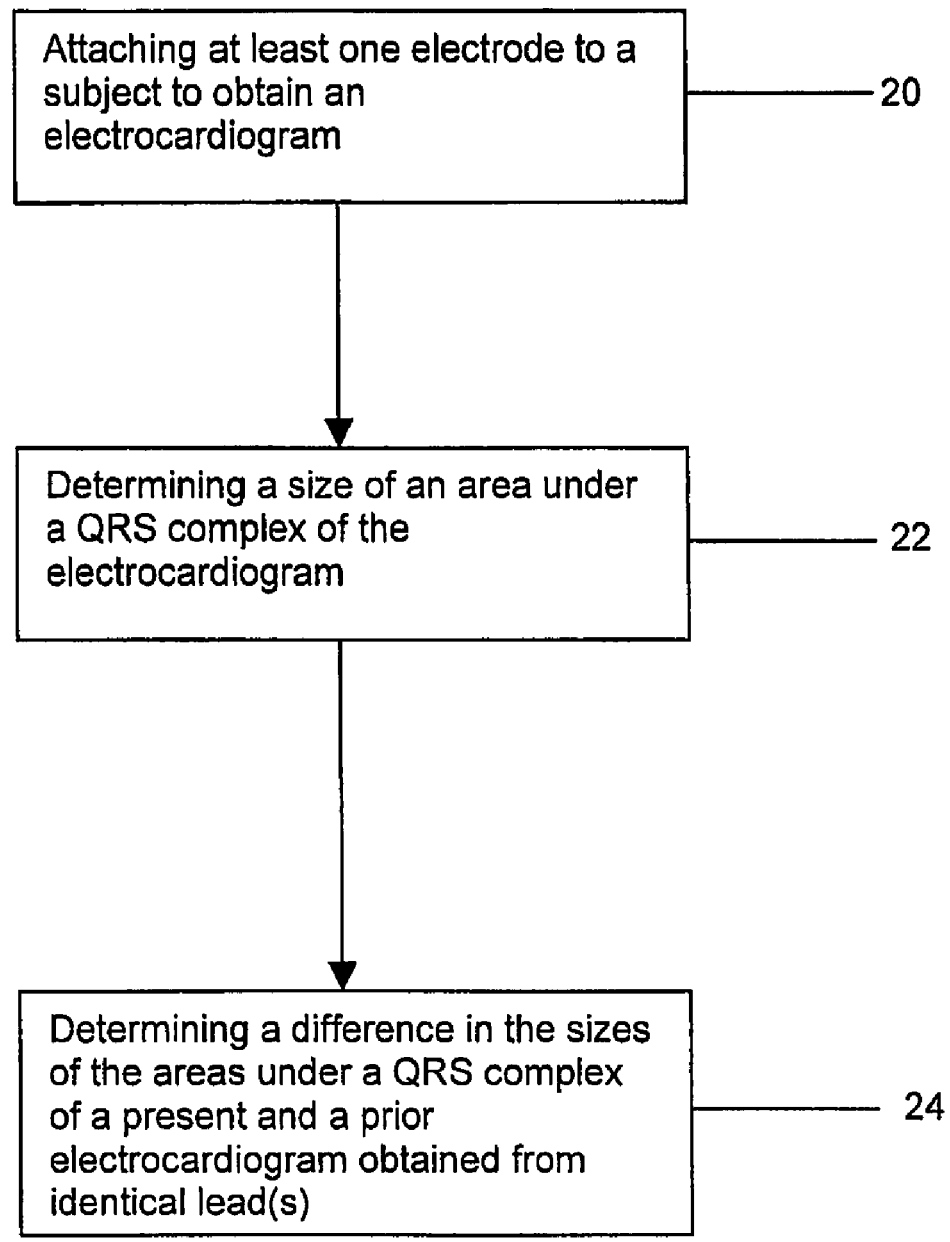
FIG. 11 shows a flow chart of a method of a preferred embodiment of the present invention.

Referring to FIG. 11, there is also provided a method for detecting a cardiac event in a subject. The subject may be a human being or an animal. Firstly, at least one electrode may be attached to the subject for obtaining an electrocardiogram of the subject's heart (20). The at least one electrode may be attached to the subject's skin or directly to the subject's heart. Referring to FIG. 12, leads V4, V5 and V6 are seen to be positioned ideally to be able to obtain readings from the left ventricle 52 of the heart and each lead may be used independently to obtain the electrocardiogram of the subject's heart. The positioning of the electrodes is per standard convention for the attainment of an electrocardiogram. Subsequent to obtaining the electrocardiogram a size of an area under a QRS complex of the electrocardiogram may be determined by visual or quantitative means (22). As described earlier, the size of the area under the QRS complex of the electrocardiogram is directly proportional to the mass of viable myocardium in the subject's heart. In addition, a difference between the size of the area of the QRS complex of the electrocardiogram and a size of an area of a QRS complex of an electrocardiogram from the same subject obtained at a prior occasion from an identical lead(s) may be determined to ascertain whether there is a change in the mass of viable myocardium in the subject's heart over a period of time (24).

Also disclosed an apparatus that is able to analyse ECGs from the same subject obtained at different times of the subject's life and determine a change in the mass of viable myocardium in the subject's heart over that period of time. The apparatus may be able to determine the difference between the size of the area of the QRS complex of the electrocardiogram and a size of an area of a QRS complex of an electrocardiogram from the same subject obtained at the prior occasion from an identical lead(s). The apparatus may comprise a computer with a scanner. A user may use software in the computer that utilises a CPU of the computer to analyse digitised images of ECGs to provide quantitative information for the user. It may also be possible for ECGs to be fed directly to and stored in the computer rather than printed on paper. The apparatus may also be a device that can be retrofitted to existing ECG machines whereby the apparatus facilitates the determination of the difference between the size of the area of the QRS complex of the electrocardiogram and a size of an area of a QRS complex of an electrocardiogram from the same subject obtained at the prior occasion. The apparatus may be in the form of an add-on data card or it may also be an externally fitted device.

Figure 14:
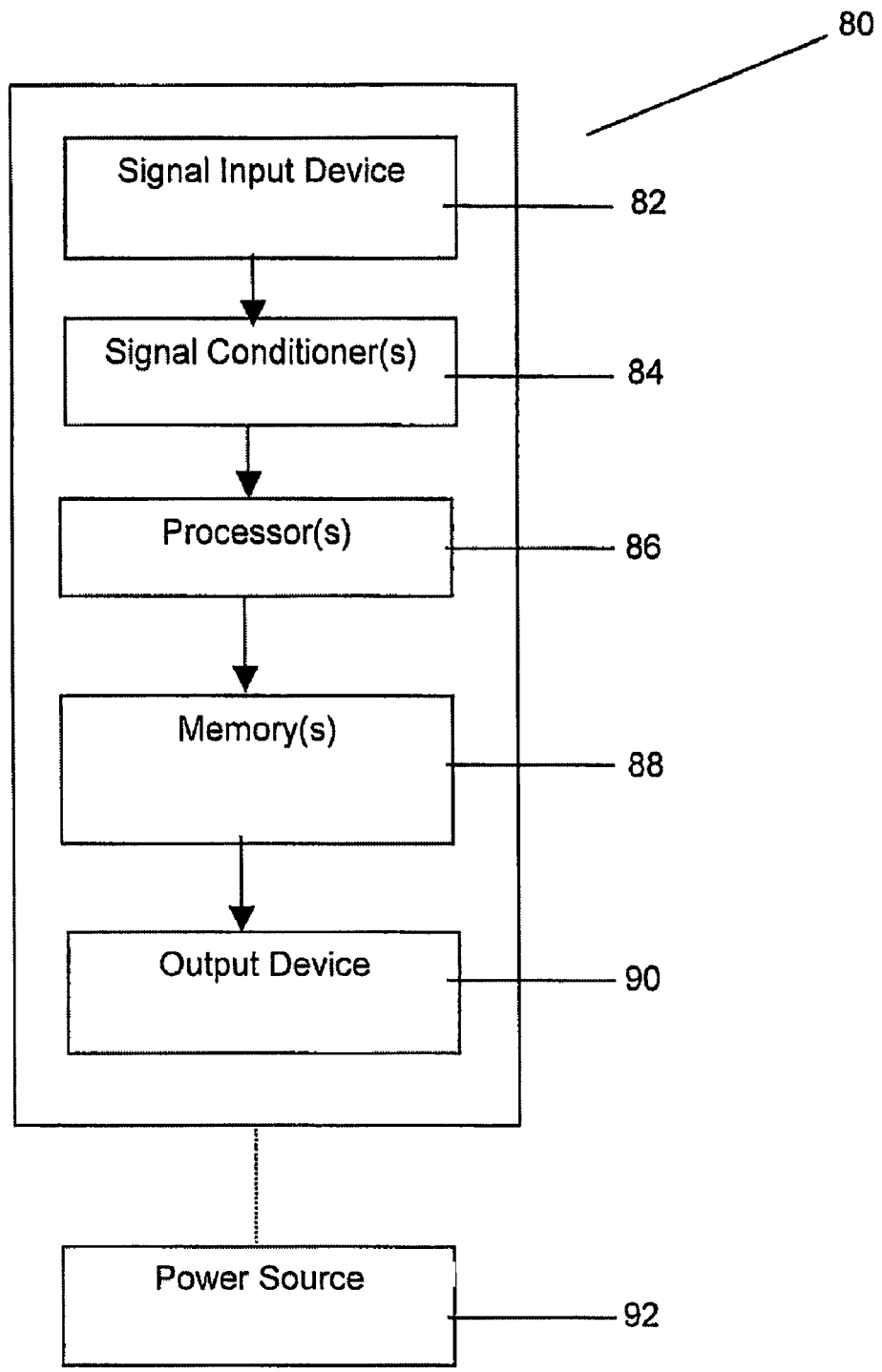
FIG. 14 shows a schematic diagram of components in an apparatus of a preferred embodiment of the present invention.
Figure 15A:
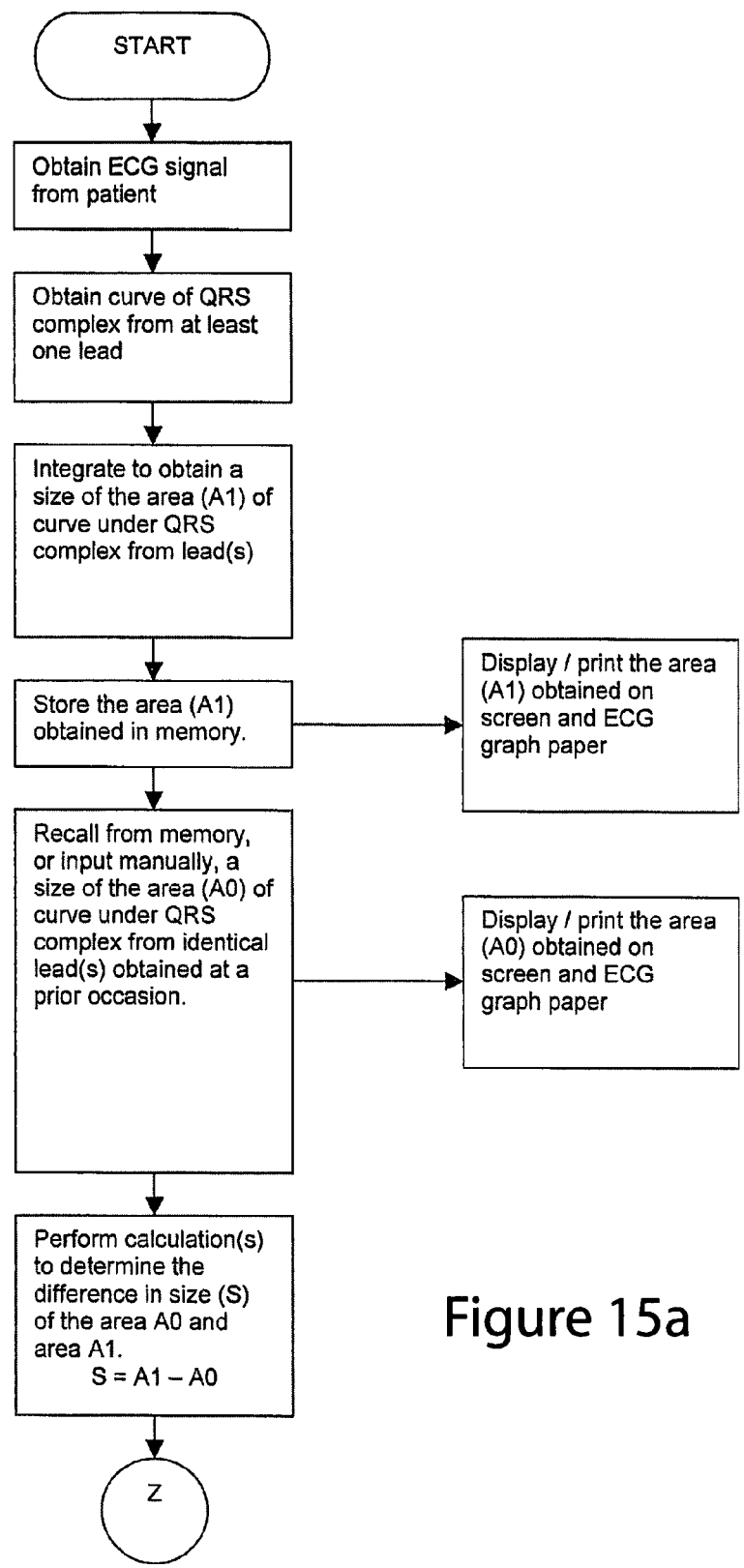
FIGS. 15a and 15b show a flow chart of a process performed by an apparatus of a preferred embodiment of the present invention.
Figure 15B:
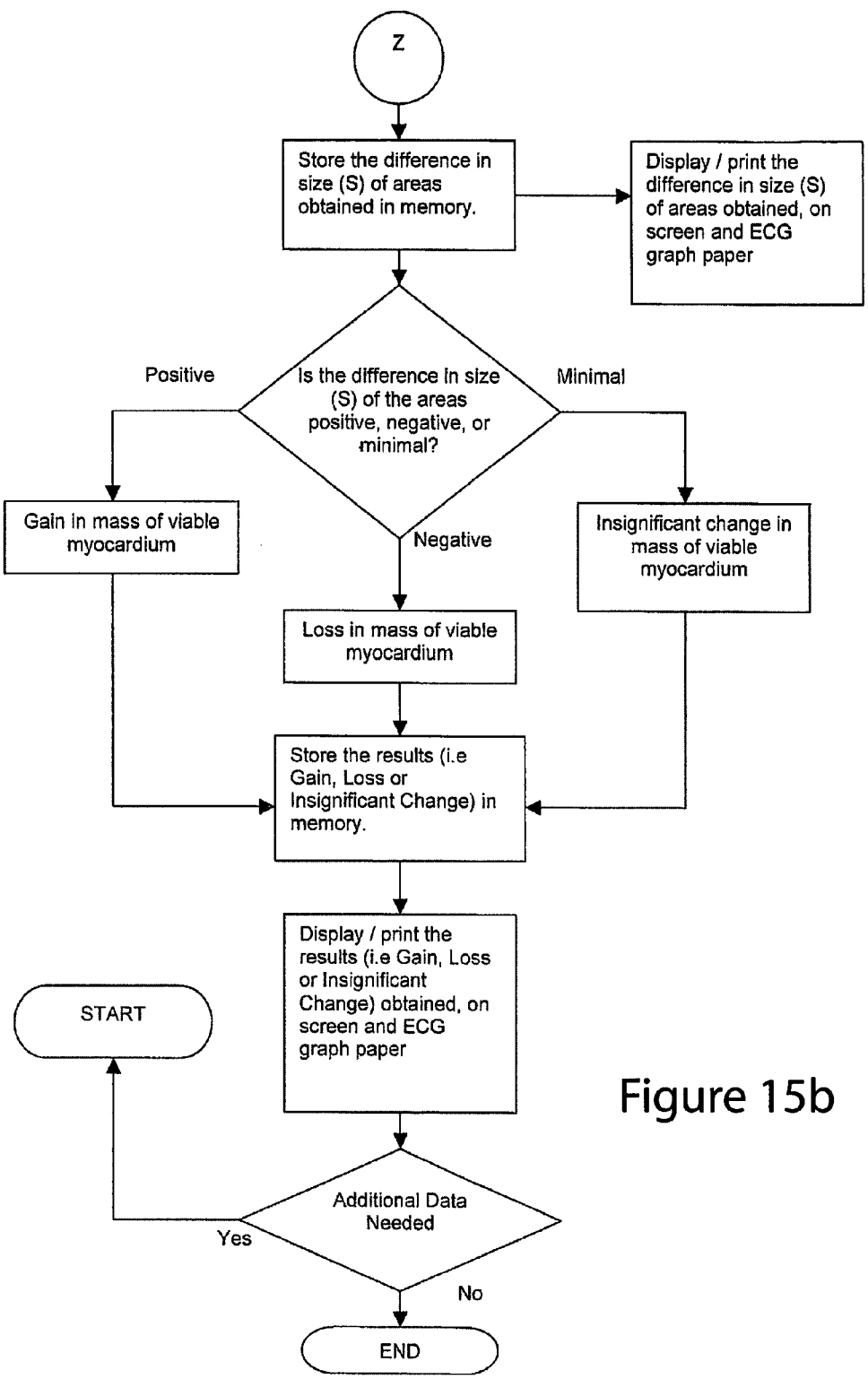

Referring to FIG. 14, there is shown a schematic diagram of the components required in the aforementioned apparatus. The apparatus 80 in the form of an add-on data card or an externally fitted device may include an input device 82 for the input of ECG signals. Subsequent to the input of signals, they are passed through a signal conditioner 84 which may include at least one digitizer before being passed into a processor 86 for signal analysis. The analysed signals are generated as data for storage in memory 88. The memory 88 may be non volatile memory. The data is then sent to an output device 90 for consumption by a user. The apparatus 80 may be powered by a separate power source 92 or may draw power directly from an ECG machine. Referring to FIG. 15, there is shown a process carried out by the apparatus 80. The process in FIG. 15 has been substantially discussed in earlier portions of the description.

In addition, there is disclosed a system for generating an index for ascertaining an onset of a cardiac event in a subject. The subject may be a human being or an animal. The system includes the attachment of at least one electrode to the subject for obtaining an electrocardiogram of the subject's heart. The at least one electrode may be attached to the subject's skin or directly to the subject's heart. Referring to FIG. 12, leads V4, V5 and V6 are seen to be positioned ideally to be able to obtain readings from the left ventricle 52 of the heart and each lead may be used independently to obtain the electrocardiogram of the subject's heart. Subsequently, a size of an area under a QRS complex of the electrocardiogram is determined to ascertain a mass of viable myocardium in the subject's heart. This may be possible as the size of the area under the QRS complex of the electrocardiogram is directly proportional to the mass of viable myocardium in the subject's heart. A difference between the size of the area of the QRS complex of the electrocardiogram and a size of an area of a QRS complex of an electrocardiogram from the same subject obtained at a prior occasion from an identical lead(s) is then obtained. After which, a quotient of the difference and the size of an area of a QRS complex of the electrocardiogram from the same subject obtained at the prior occasion is determined. As the size of the area under the QRS complex of the electrocardiogram is directly proportional to the mass of viable myocardium in the subject's heart, the difference and the quotient are correspondingly directly proportionate to one another. This allows for the generation of an index for ascertaining an onset of a cardiac event in a subject, such as, for example, degenerative cardiomyopathy, acute myocardial infarction, arrhythmia, myocardial ischaemia, and compromised ventricular function. It should be noted that the determination of the size of the area under the QRS complex of the electrocardiogram, the obtaining of the difference between the size of the area of the QRS complex of the electrocardiogram and a size of an area of a QRS complex of an electrocardiogram from the same subject obtained at a prior occasion, and the obtaining a quotient of the difference and the size of an area of a QRS complex of the electrocardiogram from the same subject obtained at the prior occasion are performed quantitatively.

Figure 13:
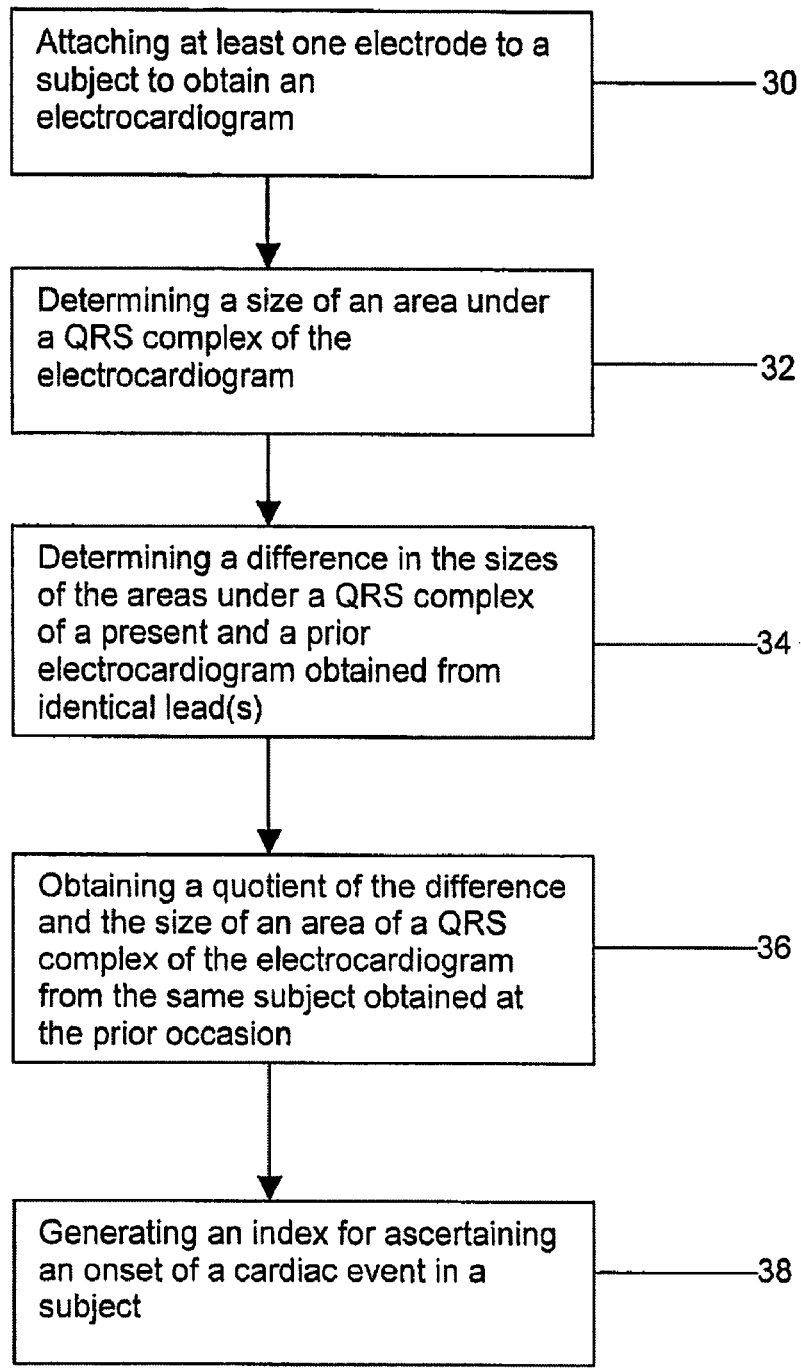
FIG. 13 shows a flow chart of a second method of a preferred embodiment of the present invention.

Referring to FIG. 13, there is similarly disclosed a method for generating an index for ascertaining an onset of a cardiac event in a subject. The subject may be a human being or an animal. Firstly, at least one electrode may be attached to the subject for obtaining an electrocardiogram of the subject's heart. (30) The at least one electrode may be attached to the subject's skin or directly to the subject's heart. Referring to FIG. 12, leads V4, V5 and V6 are seen to be positioned ideally to be able to obtain readings from the left ventricle 52 of the heart and each lead may be used independently to obtain the electrocardiogram of the subject's heart. Subsequent to obtaining the electrocardiogram a size of an area under a QRS complex of the electrocardiogram may be determined by visual or quantitative means (32). As described earlier, the size of the area under the QRS complex of the electrocardiogram is directly proportional to the mass of viable myocardium in the subject's heart. In addition, a difference between the size of the area of the QRS complex of the electrocardiogram and a size of an area of a QRS complex of an electrocardiogram from the same subject obtained at a prior occasion from an identical lead(s) may be determined to ascertain whether there is a change in the mass of viable myocardium in the subject's heart over a period of time (34). Subsequently, a quotient of the difference and the size of an area of a QRS complex of the electrocardiogram from the same subject obtained at the prior occasion is determined (36). As the size of the area under the QRS complex of the electrocardiogram is directly proportional to the mass of viable myocardium in the subject's heart, the difference and the quotient are correspondingly directly proportionate to one another and allows for the generation of the index. The index may aid in ascertaining an onset of a cardiac event in a subject, such as, for example, degenerative cardiomyopathy, acute myocardial infarction, arrhythmia, myocardial ischaemia, and compromised ventricular function. It should be noted that the determination of the size of the area under the QRS complex of the electrocardiogram, the obtaining of the difference between the size of the area of the QRS complex of the electrocardiogram and a size of an area of a QRS complex of an electrocardiogram from the same subject obtained at a prior occasion, and the obtaining a quotient of the difference and the size of an area of a QRS complex of the electrocardiogram from the same subject obtained at the prior occasion are performed quantitatively.

From an understanding of the present invention, it is foreseeable that the present invention may be applicable in the following applications:

Estimating the residual ventricular mass by comparing the ECGs of pre- and post-myocardial infarction of the same patient;

Determining the relative masses of left and right ventricles;

Following the progress of degenerative cardiomyopathies;

Following the progress of left ventricular hypertrophy in systemic hypertension and aortic stenosis;

Following the progress of right ventricular hypertrophy in cor pulmonale;

Identification of dysfunctional but viable myocardium;

Identification of irreversible myocardial damage;

Identification of candidates for fibrinolytic therapy;

Establishment of a risk-to-benefit profile for selection of candidates suitable for coronary revascularisation;

Establishment of a risk-to-benefit profile for selection of candidates suitable for coronary revascularisation to improve contractile function;

Predicting reduction in morbidity and mortality rate among heart failure when infarct region recover contractile function;

Improvement in symptoms of heart failure when infarct region recover contractile function;

Identification of patients at risk of adverse cardiac events as mass of viable myocardium decrease;

Identification of patients at risk of life-threatening arrhythmia as viable myocardium in a critically perfused region may represent a substrate for life-threatening arrhythmia;

Identification of regions of myocardial ischaemia;

Quantification of left ventricular mass, volume and function;

Establishment of myocardial viability being a binary phenomenon—segments are either viable or not. (Reason: All-or-none property of an excitable cell);

Allows for timely intervention, and hence lower operative mortality in coronary patients with poor ventricular function. (Reason: residual viability in akinetic regions tends to disappear gradually, even without recurrence of an acute coronary event);

Identification, and resultant preservation of even a small layer of viable myocardium in an infarcted region may prevent progressive remodeling and failure;

Identification and hence, optimal management of coronary artery disease, especially those with compromised ventricular function;

Quantification of viable myocardium (i.e. area under QRS Complexes) at t=0 and t=1 remains the same despite deliberate alterations in electrode positions; the heart has not suffered any cardiomyopathy progressing from time t=0 to t=1. With the deliberate shift in a given precordial lead, morphologically different QRS complexes was obtained. However, the integration, ∫QRS dt, which represents the mass of myocardium generating the electrical potentials of activation, remains unchanged;

Identification of the direct presence of viable myocytes, which provide a direct relation to myocardium viability;

Measurement of the exact quantity of viable myocytes, which provide a direct relation to myocardium viability;

Direct quantification of regional viability without technical limitations of prior art, such as SPECT, PET and DSE;

Quantification of viable myocardium, even in thin regions;

Quantification of increase or decrease of viable myocardium as a result of ventricular remodeling;

Advantage over SPECT and PET as there is an absence of partial volume effects due to poor spatial resolution;

Advantage over SPECT and PET as there is an absence of attenuation and scatter artifacts;

Advantage over DSE as there is an absence of errors in registration between comparison images;

Advantage over serum markers as there are no constraints such as specificity and sensitivity imposed by the serum markers;

An alternative method to provide information for clinical decision-making with negligible additional cost;

A readily available, non-invasive, inexpensive, and reproducible technique for providing information for clinical decision-making; and Adaptation of current ECG machines without costly enhancements/parts.

It can be seen from the above list that the present invention may have a myriad of applications in the field of cardiac medicine.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A system for detecting a cardiac event in a subject, comprising:
    a first electrode configured to be attached to a subject at a predetermined location at a first time to obtain a first electrocardiogram of a subject's heart;
    a second electrode, identical to the first electrode, configured to be attached to the subject at the predetermined location on the subject to obtain a second electrocardiogram at a second time weeks, months or years after the first time;
    memory for storing digital representations of the first and second electrocardiograms;
    a processor programmed to retrieve the first and second electrocardiograms from the memory and to compute a time-wise integral of a QRS complex of the first electrocardiogram, to compute a time-wise integral of a QRS complex of the second electrocardiogram, and to compute a difference in the time-wise integrals of the first and second electrocardiograms, wherein the difference is directly proportional to a mass of viable myocardium in the subject's heart; and
    an output device for presenting the difference to a clinician for evaluation of a change in a mass of viable myocardium of the subject's heart.

2. The system of claim 1, wherein the first and second electrodes are configured to be attached to the subject's skin.

3. The system of claim 1, wherein the first and second electrodes are configured to be attached to the subject's heart.

4. The system of claim 1, wherein the difference presented by the output device may be used by the clinician to determine the occurrence of a cardiac event selected from the group consisting of: degenerative cardiomyopathy, acute myocardial infarction, acute coronary syndrome, arrhythmia, myocardial ischemia, and compromised ventricular function.

5. The system of claim 1, wherein the difference presented by the output device is a positive value, corresponding to a gain in the mass of viable myocardium in the subject's heart.

6. The system of claim 1, wherein the difference presented by the output device is a negative value, corresponding to a loss in the mass of viable myocardium in the subject's heart.

7. The system of claim 1, wherein the output device presents the difference in a: visual or quantitative manner.

8. The system of claim 1, wherein the subject is selected from a group consisting of: human being and animal.

9. A method for detecting a cardiac event in a subject, comprising the steps of:
    at a first time, attaching a first electrode to a subject at a predetermined location to obtain a first electrocardiogram from the subject's heart;
    at a second time weeks, months or years after the first time, attaching a second electrode, identical to the first electrode, to the subject at the predetermined location to obtain a second electrocardiogram from the subject's heart;
    computing a time-wise integral of a QRS complex of the first electrocardiogram;
    computing a time-wise integral of a QRS complex of the second electrocardiogram;
    computing a difference in the time-wise integrals of the first and second electrocardiograms; and
    evaluating the difference to determine occurrence of a change in a mass of viable myocardium in the subject's heart.

10. The method of claim 9, wherein the first and second electrodes are attached to the subject's skin.

11. The method of claim 9, wherein the first and second electrodes are attached to the subject's heart.

12. The method of claim 9, wherein evaluating the difference determines occurrence of a cardiac event is selected from the group consisting of: degenerative cardiomyopathy, acute myocardial infarction, acute coronary syndrome, arrhythmia, myocardial ischemia, and compromised ventricular function.

13. The method of claim 9, wherein evaluating the difference as a positive value corresponds to determining a gain in the mass of viable myocardium in the subject's heart.

14. The method of claim 9, wherein evaluating the difference as a negative value corresponds to determining a loss in the mass of viable myocardium in the subject's heart.

15. The method of claim 9, wherein evaluating the difference comprises evaluating visual or quantitative information.

16. The method of claim 9, wherein the subject is selected from a group consisting of: human being and animal.

17. A system for detecting a cardiac event in a subject by comparing ECGs obtained at different times, comprising:
   an input device configured to accept first and second electrocardiograms of a subject's heart, the first electrocardiogram generated at a first time with at least a first electrode positioned at a predetermined location on the subject, the second electrocardiogram generated at a second time weeks, months or years after the first time, with a second electrode positioned at the predetermined location on the subject;
   memory for storing digital representations of the first and second electrocardiograms;
   a processor programmed to retrieve the first and second electrocardiograms from the memory and to compute a time-wise integral of a QRS complex of the first electrocardiogram, to compute a time-wise integral of a QRS complex of the second electrocardiogram, and to compute a difference in the time-wise integrals of the first and second electrocardiograms, wherein the difference is directly proportional to a mass of viable myocardium in the subject's heart; and
   an output device for presenting the difference to a clinician for evaluation.

18. The system of claim 17, wherein the difference presented by the output device may be used by the clinician to determine the occurrence of a cardiac event selected from the group consisting of: degenerative cardiomyopathy, acute myocardial infarction, acute coronary syndrome, arrhythmia, myocardial ischemia, and compromised ventricular function.

19. The system of claim 17, wherein the difference presented by the output device is a positive value, corresponding to a gain in the mass of viable myocardium in the subjects heart.

20. The system of claim 17, wherein the difference presented by the output device is a negative value, corresponding to a loss in the mass of viable myocardium in the subject's heart.

21. The system of claim 17, wherein the output device presents the difference in a visual or quantitative manner.

22. The system of claim 17, wherein the first and second electrocardiograms comprise paper strips, the system further comprising a scanner for scanning the paper strips.

23. The system of claim 22, further comprising a digitizer for converting information contained on the paper strips into digital values that may be stored in the memory.

24. The system of claim 17, further comprising first and second identical electrodes, the first and second electrodes configured to be used at the first and second times, respectively.

25. The system of claim 24, wherein the first and second electrodes are configured to be attached to the subject's skin.

26. The system of claim 24, wherein the first and second electrodes are configured to be attached to the subject's heart.

* * * * *